(12) United States Patent  (10) Patent No.: US 7,400,410 B2
Baker et al.  (45) Date of Patent: Jul. 15, 2008

(54) OPTICAL COHERENCE TOMOGRAPHY FOR EYE-LENGTH MEASUREMENT

(75) Inventors: Chris Baker, Moraga, CA (US); Matthew J. Everett, Livermore, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 401 days.

(21) Appl. No.: 11/243,665

(22) Filed: Oct. 5, 2005

(65) Prior Publication Data

US 2007/0076217 A1  Apr. 5, 2007

(51) Int. Cl.
G01B 11/02 (2006.01)
G01B 9/02 (2006.01)
A61B 3/14 (2006.01)

(52) U.S. Cl. .................. 356/498; 356/497; 356/482; 351/210

(58) Field of Classification Search .......... 356/479, 356/497, 498, 482; 351/209, 210
See application file for complete search history.

(56) References Cited

U.S. PATENT DOCUMENTS

| | | | | |
|---|---|---|---|---|
| 4,796,989 A | * | 1/1989 | Fukuma et al. | 351/212 |
| 4,859,051 A | * | 8/1989 | Fukuma et al. | 351/211 |
| 4,938,584 A | | 7/1990 | Suematsu et al. | 351/211 |
| 5,141,302 A | * | 8/1992 | Arai et al. | 351/205 |
| 5,321,501 A | | 6/1994 | Swanson et al. | 356/479 |
| 5,329,321 A | | 7/1994 | Koizumi | 351/205 |
| 5,347,327 A | * | 9/1994 | Sekine et al. | 351/211 |
| 5,347,328 A | * | 9/1994 | Sekine et al. | 351/211 |
| 5,349,399 A | * | 9/1994 | Sekine | 351/215 |
| 5,387,951 A | * | 2/1995 | Hatanaka | 351/205 |
| 5,491,524 A | | 2/1996 | Hellmuth et al. | 351/212 |
| 5,633,694 A | | 5/1997 | Mihashi et al. | 351/211 |
| 5,673,096 A | * | 9/1997 | Dorsel et al. | 351/211 |

(Continued)

FOREIGN PATENT DOCUMENTS

WO  WO 01/38820 A1  5/2001

(Continued)

OTHER PUBLICATIONS

A. Baumgartner et al., "Signal and Resolution Enhancements in Dual Beam Optical Coherence Tomography of the Human Eye," *Journal of Biomedical Optics*, vol. 3, No. 1, Jan. 1998, pp. 45-54.

(Continued)

Primary Examiner—Patrick J Connolly
(74) Attorney, Agent, or Firm—Stallman & Pollock LLP

(57) ABSTRACT

An accurate measure of eye length can be obtained using concurrent OCT measurements. A position OCT device can be used to continually monitor the position of the front surface of the cornea, while a distance OCT device can determine the apparent distance between the front surface of the cornea and the front surface of the retina. Since the eye is likely to move during the period of time between measurements of the cornea and retina, the monitored position of the cornea can be used to correct the apparent length measurement by the amount of eye movement over that period of time, in order to obtain an accurate measure of eye length. In some embodiments a single OCT device can serve the dual role of monitoring eye position while making eye length measurements.

25 Claims, 7 Drawing Sheets

U.S. PATENT DOCUMENTS

| | | | | |
|---|---|---|---|---|
| 5,847,827 | A | * | 12/1998 | Fercher ...................... 356/493 |
| 5,975,697 | A | | 11/1999 | Podoleanu et al. .......... 351/206 |
| 5,975,699 | A | | 11/1999 | Hellmuth .................... 351/211 |
| 6,053,613 | A | | 4/2000 | Wei et al. .................... 351/205 |
| 6,099,522 | A | * | 8/2000 | Knopp et al. ................. 606/10 |
| 6,775,007 | B2 | | 8/2004 | Izatt et al. ................... 356/497 |
| 7,084,986 | B2 | * | 8/2006 | Hellmuth et al. ............ 356/479 |
| 2004/0061830 | A1 | * | 4/2004 | Hellmuth et al. ............ 351/205 |
| 2005/0140981 | A1 | | 6/2005 | Waelti ........................ 356/479 |
| 2005/0203422 | A1 | * | 9/2005 | Wei ............................ 600/476 |
| 2007/0002277 | A1 | * | 1/2007 | Hanebuchi .................. 351/206 |
| 2007/0177104 | A1 | * | 8/2007 | Lacombe et al. ............ 351/211 |

FOREIGN PATENT DOCUMENTS

WO     WO 2005/033624 A1     4/2005

OTHER PUBLICATIONS

W.J.O. Boyle et al., "Optical instrumentation for eye length measurement using a short coherence length laser-based interferometer approach," *Rev. Sci. Instrum.*, vol. 64, No. 11, Nov. 1993, pp. 3082-3087.

S. Chen et al., "A Compact Optical Device for Eye-Length Measurement," *IEEE Photonics Technology Letters*, vol. 5, No. 6, Jun. 1993, pp. 729-731.

A.F. Fercher et al. "Measurement of optical distances spectrum modulation," *SPIE*, vol. 2083 (1994), pp. 263-267.

A.F. Fercher et al., "Eye-length measurement by interferometry with partially coherent light," *Optics Letters*, vol. 13, No. 3, Mar. 1988, pp. 186-188.

A.F. Fercher et al., "Ophthalmic laser interferometry," *Optical Instrumentation for Biomedical Laser Applications—SPIE*, vol. 658 (1986), pp. 48-51.

T. Hellmuth et al., "Non-contact measurement of the optical imaging quality of an eye," *Photon Migration, Optical Coherence Tomography, and Microscopy—Proceedings of SPIE*, vol. 4431 (2001), pp. 52-58.

C.K. Hitzenberger et al., "In vivo intraocular ranging by wavelength tuning interferometry," *Coherence Domain Optical Methods in Biomedical Science and Clinical Applications II—SPIE*, vol. 3251 (1998), pp. 47-51.

C.K. Hitzenberger et al., "Measurement of the axial eye length and retinal thickness by laser Doppler interferometry (LDI)," *Holography, Interferometry, and Optical Pattern Recognition in Biomedicine—SPIE*, vol. 1429 (1991), pp. 21-25.

C.K. Hitzenberger, "Optical Measurement of the Axial Eye Length by Laser Doppler Interferometry," *Investigative Ophthalmology & Visual Science*, vol. 32, No. 3, Mar. 1991, pp. 616-624.

F. Lexer et al., "Wavelength-tuning interferometry of intraocular distances," *Applied Optics*, vol. 36, No. 25, Sep. 1, 1997, pp. 6548-6553.

A.Gh. Podoleanu et al., "Fiberised set-up for eye length measurement," *Optics Communications*, vol. 137 (1997) pp. 397-405.

G.F. Schmid, "Axial and peripheral eye length measured with optical low coherence reflectometry," *Journal of Biomedical Optics*, vol. 8, No. 4, Oct. 2003, pp. 655-662.

A. Sekine et al., "Axial eye-length measurement by wavelength-shift interferometry," *J. Opt. Soc. Am. A*, vol. 10, No. 7, Jul. 1993, pp. 1651-1655.

D.N. Wang et al., "A low coherence 'white light' interferometric sensor for eye length measurement," *Rev. Sci. Instrum.*, vol. 66, No. 12, Dec. 1995, pp. 5464-5468.

D.N. Wang et al., "The Use of Short Coherence Length Laser Light for Eye Length Measurement," *Engineering in Medicine and Biology Societ (vol. 14)—Proceedings of the Annual International Conference of the IEEE*, vol. 1 (1992), pp. 340-341.

In re U.S. Appl. No. 10/933,795, filed Sep. 3, 2004, by Matthew J. Everett et al., entitled "Patterned Spinning Disk Based Optical Phase Shifter for Spectral Domain Optical Coherence Tomography," 53 pages in length.

* cited by examiner

At time t1:

At time t2:

OPTICAL COHERENCE TOMOGRAPHY FOR EYE-LENGTH MEASUREMENT

TECHNICAL FIELD OF THE INVENTION

The present invention relates to optical techniques useful for measuring dimensions of a moveable living sample such as a human eye.

BACKGROUND

In industrial, medical, and various other applications, it often is necessary to make measurements at a resolution of less than 10 microns. This becomes especially difficult for samples, such as living samples, that are likely to move during the measurement(s). A particular problem arises when measuring dimensions of the eye, as the eye is highly likely to move between a pair of measurements taken on, for example, the front and back surfaces of the eye. One technology that has been used to measure eye-length is Optical Coherence Tomography (OCT), such as is described in U.S. Pat. No. 5,321,501, which is hereby incorporated herein by reference. OCT is a non-invasive, real-time imaging technique capable of obtaining images and making measurements on the order of about 10 microns or less.

Several variations of OCT systems have been used with varying results. One such variation is a time-domain OCT (TD-OCT) system. A TD-OCT system typically uses a standard Michelson interferometer-based approach, such as is described in U.S. Pat. Nos. 5,329,321 and 5,387,951 for a full reference path scan. In applications such as measuring eye lengths, it is desirable to form high-resolution axial scans of the front and rear portions of the eye, but there is little value to scanning the center of the eye. A long axial scan covering the entire length of the eye, with the desired axial resolution throughout the scan, would spend considerable time scanning through the center of the eye, during which the eye may move and during which time little or no valuable information is being collected. Therefore a system is desired that is capable of separate high-resolution scans of the front and rear portions of the eye. U.S. Pat. Nos. 6,053,613 and 6,775,007 and Publication No. 2005/0140981 describe OCT systems with dual reference paths and a short-range reference-path scan. All of these references are hereby incorporated herein by reference. FIG. 1 shows a basic full range reference path length scan system, wherein light from a low coherence source 102 is input into a beam splitter 104. The beam splitter directs the light along two arms, namely a measurement arm 106 and a reference arm 108. An optical fiber 110 in the measurement arm 108 extends into a device 112 that scans an eye 114 with a beam of light. The reference arm 106 provides a variable optical delay using light reflected back by a reference mirror 116. A piezoelectric modulator based path length stretcher 118 can be included in the reference arm 106 with a fixed reference mirror 116 to either change the path length or to create a modulation or beating frequency, and the reference mirror 116 can be a scanning mirror such that the mirror can be scanned in the direction of the incoming beam, shown in the figure as the Z-direction. The reflected reference beam from the reference arm 106 and the scattered measurement beam from the sample arm 108 pass back and combine through the splitter 104 to a detector device 120, including processing electronics, which can process the signals using techniques known in the art. The processed signals can be used to give a measurement of eye length, as well as to produce a backscatter profile or image on a display unit 122. Due to the need for the reference mirror to move, measurements may not be accurate since the position of the eye can change while the mirror is moving.

Another variation is a spectral domain OCT (SD-OCT) device, such as is described in U.S. Pat. No. 5,975,699, which is hereby incorporated herein by reference. An exemplary SD-OCT device uses a spectral interferometer, where light from a source such as a superluminescent diode (SLD) can be reflected from surfaces of the eye, the eye reflected light is combined with a reference light and is focused onto a spectrometer, where the resulting spectrum can be analyzed as known in the art. A problem with such an approach is that the depth range that can be covered in such a system is typically limited (by the spectral resolution of the spectrometer) to a few millimeters, such as 3-4 mm for a typical A-scan, which is not sufficient to cover the full length of the eye (an optical path length typically equivalent to 28 mm to 35 mm in air). Thus, measuring the eye length with a typical SD-OCT system requires two separate measurements between which the reference arm is moved by approximately the length of the eye. Since the eye can move during those two measurements, error can be introduced. A similar problem is encountered when using a swept-source OCT (SS-OCT) device that varies the wavelength of the light source, such as is described in U.S. Pat. Nos. 5,347,327 and 5,347,328, which are hereby incorporated herein by reference.

There are many other variations of these OCT devices, each of which suffers the same problem of eye movement during the measurement process. When using an interferometer to measure the relative positions in space of the "front" and "back" surface of the eye, here the front surfaces of the cornea and retina, respectively, it can take on the order of about ¾ second between the front and back measurements. This leads to the probability of movement. For high-precision applications such as cataract surgery, where a lens of the appropriate focal length is inserted in the eye, an error in measurement due to movement of just 100 microns produces an intolerable error of approximately 0.25 diopters in lens prescription, so it is critical to know the correct eye length (as used in industry, the distance from the front surface of the cornea to the front surface of the retina). Existing OCT systems therefore are not sufficient to measure this critical dimension.

DETAILED DESCRIPTION

Systems and methods in accordance with various embodiments of the present invention can overcome deficiencies in existing optical measurement systems by accounting for the movement of the eye during the measurement process. In at least one embodiment, a secondary optical approach is used to measure the movement of the eye during the time in which optical dimension measurements are being made by a primary optical approach. The amount of eye movement then can be used to adjust the dimension measurements, in order to produce more accurate results than are possible with existing OCT systems. It should be understood that such technique can be used for any other appropriate sample that is likely to move during the measurement process.

In one embodiment, separate sets of optical coherence tomography (OCT) measurements can be taken concurrently. These measurements can be made using any of a number of OCT techniques, including TD-OCT, SD-OCT, and SS-OCT. A first set of OCT measurements can be used to monitor the position of the cornea relative to an absolute reference. A second set of OCT measurements can be used to determine the relative positions of the cornea and the retina. This second set of measurements, however, is susceptible to eye movement as discussed above. Using only the second set of measurements then would yield only an apparent eye length. By concurrently measuring the axial (along the axis of the measurement beam) movement of the eye during the measurement process, an actual eye length can be calculated by adjusting the apparent length (second OCT set) by the amount of axial movement (first OCT set).

Figure 1:
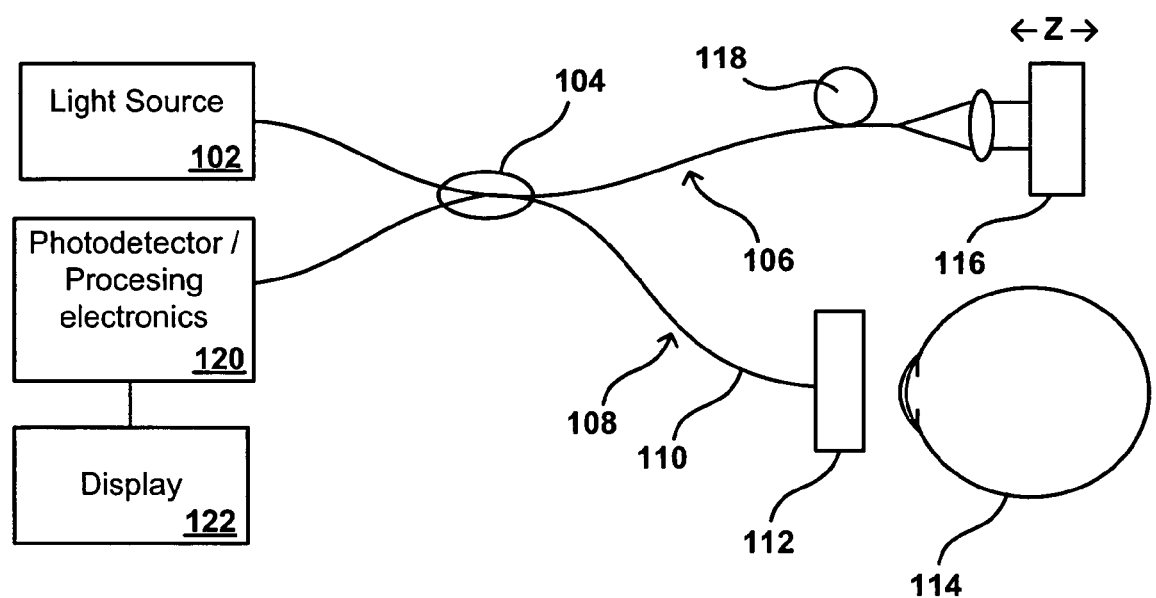
FIG. 1 is a diagram of a first OCT system of the prior art.
Figure 2:
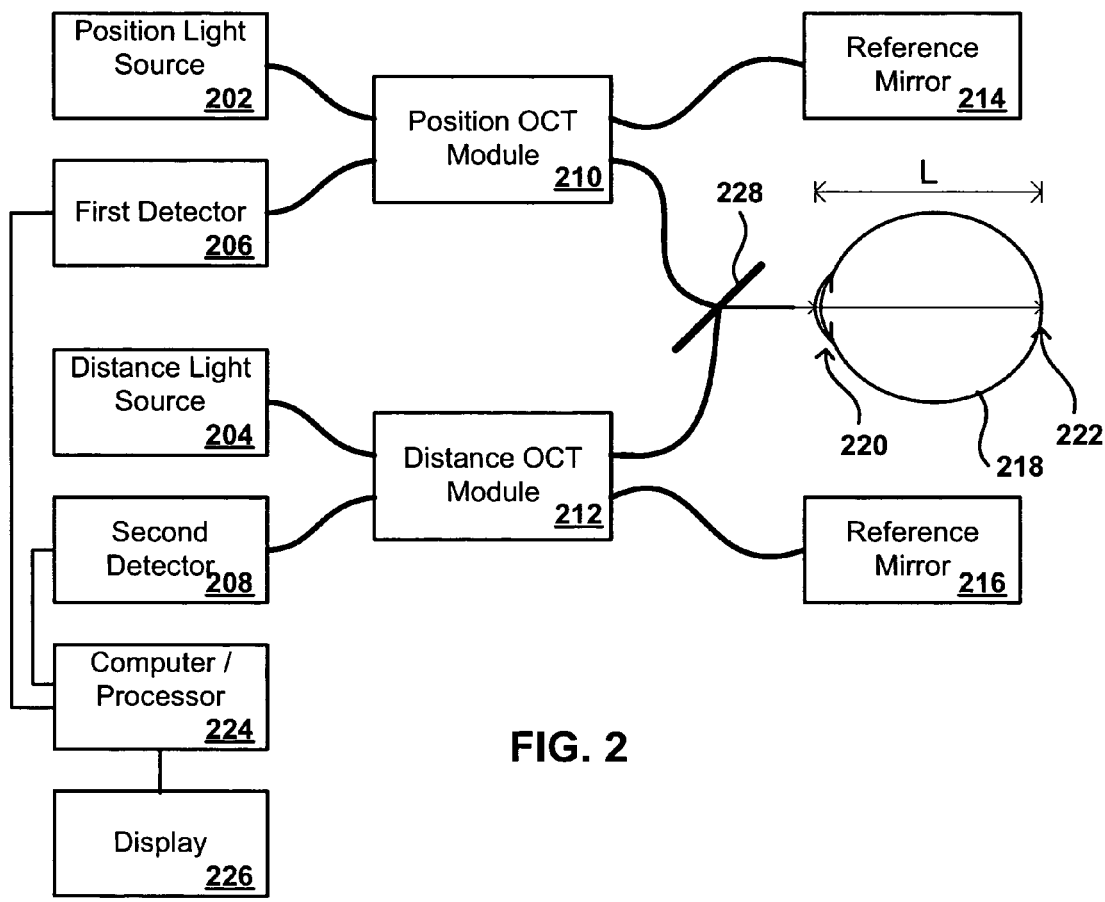
FIG. 2 is a diagram of a dual-measurement OCT system in accordance with one embodiment of the present invention.

A system including components for making concurrent OCT measurements in accordance with one embodiment of the present invention is shown in FIG. 2. In this exemplary OCT system 200, a position optical source 202 such as a first SLD provides infrared (IR) light at about 1300 nm, and a distance optical source 204 such as a second SLD provides IR light at about 840 nm. The 1300 nm light can be used to measure the position of the surface of the cornea, as wavelengths around 1300 nm are absorbed by water and aqueous solutions. This absorption allows the 1300 nm light to be very intense without passing through the liquid part of the eye to damage the retina. The ability to run at a higher intensity avoids problems in the prior art with signal-to-noise ratio. The 840 nm light, which can penetrate the lens and the aqueous portion of the eye, can have an effective path length that is adjustable over a range that allows the positions of the front surface of the cornea and the front surface of the retina to be measured, such that the distance between them can be determined.

Although SLDs producing light at 1300 nm and 840 nm may be desirable in this embodiment, the light sources generally can be any appropriate light sources capable of producing broadband light with a center wavelength within the spectrum range from ultra-violet to near infrared. Exemplary sources can also include a light emitting diodes (LEDs) and short pulsed lasers. For some systems the bandwidth of a short pulsed laser might be too broad, but might be acceptable for systems including SD-OCT devices. These lasers can be expensive, however, and may not produce an accurate enough wavelength. Each source in this embodiment can have a bandwidth of at least 5 nm, but larger bandwidths can be used to obtain improved resolution.

The light from each light source can be directed, such as via a fiber, into a respective OCT module 210, 212, which can include elements such as a splitter to split the light beams along reference and measurement arms and recombine light reflected back along those arms, as well as other elements comprising an interferometer as known in the art. OCT modules and devices also can include various other components known in the art for use with an OCT device, such as optical detection elements, electronics, motors, controller(s), and processors. Each OCT module also can contain devices for transmitting outgoing light beams and/or detecting each reflected light beam. Each module can include any appropriate optical element(s) known in the art for combining light beams of different wavelengths, where necessary.

For each OCT module, the outgoing light can be split into paths along a reference arm, going either between the module and a reference mirror device or through a transmissive path, and a measurement arm going between the module and the eye (or other sample). For example, the light from the position light source 202 is directed to a first OCT module 210, which directs a portion of the 1300 nm light to a first reference mirror 214 and a portion of the light to the eye 218. The light from the distance light source 204 is directed to a second OCT module 212, which directs a portion of the 840 nm light to a second reference mirror 216 and a portion to the eye 218. A dichroic mirror 228 or other appropriate element or device can be used to combine the respective portions of the position and distance beams and direct the combined beams toward the eye. Combining the light along a common path allows for a more accurate measurement of eye movement during the measurement for points along the beam path. In systems where the beams of light have different polarizations instead of, or in addition to, different wavelengths, an element such as a polarization beam splitter/combiner can be used in place of a dichroic mirror or similar element. Any arm or path in the system can include an optical fiber for directing the light. The fibers can include any appropriate fiber, such as a single mode optical fiber of approximately 5 microns in diameter for carrying infrared light. Each imaging arm also can include optical elements and/or lens assemblies for performing a variety of imaging functions as known in the art. In an alternative embodiment, the light beams from each OCT module 210, 212 can be directed separately to the eye 218. While it can be desirable to co-align the beams since a pupil is relatively small, there can be enough space to offset the beams by an appropriate amount. A potential advantage to using separate paths is that a single source can be used, since the separated beams can have the same wavelength.

The portion of the light (here the 1300 nm light) from the position optical source 202 directed to the reference mirror can be scanned an axial distance on the order of a few millimeters by varying the path length of the 1300 nm reference beam (for a TD-OCT device). This scanning can be done in one embodiment at a frequency of about 1000 Hz. The reference mirror 214 can be used to vary the path length, such as by using a moveable reference reflector or piezoelectric modulator based fiber stretcher (with a fixed reference mirror), as well as other approaches known in the art. By controlling the reference reflector, for example, the path length of light reflected back from the mirror can be adjusted and controlled. The reference mirror 216 for the distance light source 204, here the 840 nm light, also can vary the path length by an amount to measure the positions of the cornea and retina, such as an amount on the order of about 50 mm in air at a speed of about 75 mm per second. Each reference reflector can be a moveable mirror or retro-reflector, such as a reflector on a translation stage. To achieve high scan rates on the order of 2000 Hz for the position reference path, alternate methods such as a rapid scanning optical delay line (RSOD) can be used.

Scanning the position reference path over a few millimeters allows for some movement of the eye in either direction along the scan direction, while providing enough scan points (due to. the higher possible frequency) to ensure an adequate position measurement for the cornea at any point during the measurement process. The scan frequency can be high enough to monitor eye movements with an accuracy of about 2 microns, which is sufficient since the maximum amount of eye movement between scans is on the order of about 2 mm/sec. There are many other ways to vary a reference path length, such as by using a spinning disk/snail shell approach as known in the art. Any appropriate method for varying path length that is known or used in the art can be used in accordance with the various embodiments.

A portion of the 1300 nm and 840 nm light directed to the eye will be reflected back to the position OCT 210 and distance OCT 212 modules, respectively. Whenever the respective reference path length is matched to the path length to the feature being measured (position device), or one of the scattering microstructures in the eye (distance device), an interference fringe will be generated. As each reference mirror device 214, 216 scans across the respective path range, fringes will appear for each depth at which light is scattered from the eye. The fringes can be used to determine position, and thus distance, as known in the art. The envelope formed by these fringes then corresponds to the scattering profile for the eye. A 30 nm bandwidth light source can be used to scan the eye in one embodiment, which corresponds to a coherence length of about 10 microns. Other ways for determining distance using an OCT module are known in the art and will not be described in detail herein.

Each OCT device can utilize a detector device 206, 208, such as may contain a photodetector or other detection element, for use in making precise measurements of time delay and magnitude of the light that is reflected and/or scattered by the eye. Each detector can detect the fringes produced through the interference of the reference and measurement light beams for each OCT module, and can generate at least one output signal in response thereto. The signal from each detector 206, 208 can be received by a computer 224 or processor, capable of using the timing information and the interference data to determine the amount of axial movement of the eye, using the signal from detector 206, as well as the apparent distance between the cornea and the retina, using the signal from detector 208. The computer can adjust the apparent length of the eye by the amount of axial movement of the eye during the measurement period. Since the timing of reference points captured by the distance detector 206 may not correspond exactly with the timing of the measurement points captured for the cornea and the retina by distance detector 208, the computer can use any appropriate hardware and/or software to interpolate the position of the eye between each point in order to obtain a more accurate measurement of eye movement during the measurement period. Methods for interpolating between data points are well known in the art and will not be discussed in detail herein. The resultant measurement data can be stored to memory, and can be printed or displayed to a user through an appropriate display device 226, such as a standard computer monitor.

The OCT modules, as well as any positioning or scanning controller, can be controlled by a control computer module that is responsible for synchronization, generating drive waveforms, generating necessary trigger pulses, storing and recalling data, and/or performing any necessary signal and image processing. The control computer module can function as part of the display module, as the display module can receive data from the computer module and/or directly from the OCT modules. OCT images and information can be displayed simultaneously with, or merged with, other imaging modalities such as ultrasound or MRI to permit real-time guidance and placement. In. addition to information provided by the OCT imaging system, such visualization techniques will permit other critical data to be analyzed, for example, permitting retrieval of previously acquired images and access to patient records while a measurement or procedure is being performed.

An exemplary approach to measuring eye length using a TD-OCT system such as one described with respect to FIG. 2 will be described with respect to FIG. 3. At a first time ($t_1$), a first OCT device can measure the relative position of the front surface of the cornea 306, denoted in FIG. 3(*a*) as position $X_1$. The position of the front surface can be determined using an OCT process as described above. A second OCT device also can measure the relative position of the cornea at time $t_1'$, this position designated in FIG. 3(*a*) as position $L_1$. The OCT devices can be triggered to monitor the cornea position at approximately the same time, but there typically will be some difference between the times at which each scan actually hits the surface of the cornea. The first OCT device can be running continuously, such that a value for $X_1$ is registered at approximately the same time as the reference beam path length of the second OCT device crosses the value corresponding to front surface of the cornea at time $t_1'$, such as a time immediately before or after $t_1$, occurs. In one embodiment $t_1'$ occurs just after $t_1$, as the timing or $t_1$ is used to trigger the capture at time $t_1'$. There can be a finite amount of time between the occurrence of $t_1$ and $t_1'$, which is typically comparable to the inverse of the scan rate. The preferred scan rate of approximately 1000 Hz corresponds to approximately 1 millisecond between $t_1$, and $t_1'$, during which time the human eye moves typically less than 2 microns.

As the second OCT device scans the eye 300, there can be significant interference registered at a number of locations, such as: the rear surface of the cornea 306, the front surface of the lens 302, the rear surface of the lens 302, and the front surface of the retina 310. The measurement beam can have a small enough diameter that there is no interference due to the iris 304, and can be of a wavelength capable of penetrating the aqueous center 308 of the eye as discussed above. Since there is a significant distance between the back of the lens and the retina, the selection of the interference signal that correctly coincides with the location of the retina can be obtained by setting a window, such as a range (in air) of approximately $L_1+15$ mm to approximately $L_1+40$ mm. At the instant the second OCT device registers interference from the front surface of the retina, the exact time of the event $t_2$ can be determined and the second OCT device can interrogate an internal precision scale to obtain the relative retinal position $L_2$. Since the first OCT device is running continuously, the position of the front surface of the cornea $X_2$ can be registered as the reference beam path length crosses the value corresponding to the front surface of the cornea at time $t_2'$. As discussed above with respect to $t_1'$, $t_2'$ can occur at approximately the same time as $t_2$, such as immediately after time $t_2$ occurs. The exact position of $X_2$ can be refined using interpolation, as described earlier, to more accurately predict the location of $X_2$ when time $t_2$ actually occurred.

A computer or other processing device can determine the amount of axial movement of the eye from time $t_1$, to time $t_2$ by comparing the relative positions of $X_1$ and $X_2$. The apparent length of the eye can be determined by comparing the relative values of $L_1$ and $L_2$. In order to compensate for the movement during the measurement period to obtain an accurate measurement of eye length, the apparent length can be adjusted by the amount of movement to obtain an eye length measurement given by:

$$\text{Length} = (L_2 - L_1) - (X_2 - X_1)$$

It should be understood that there are other time variations, as the values for the position of the front surface of the cornea can be taken before, during, or after the first eye length measurement and/or second eye length measurement. While it may be stated herein that the position of movement of the eye occurs for the measurement period, it is intended that the measurements or monitoring of position occur around the time of measurement, such that a reasonable estimate can be made of the amount of movement along the measurement path that the eye made between the first and second eye length measurements.

Figure 3A:
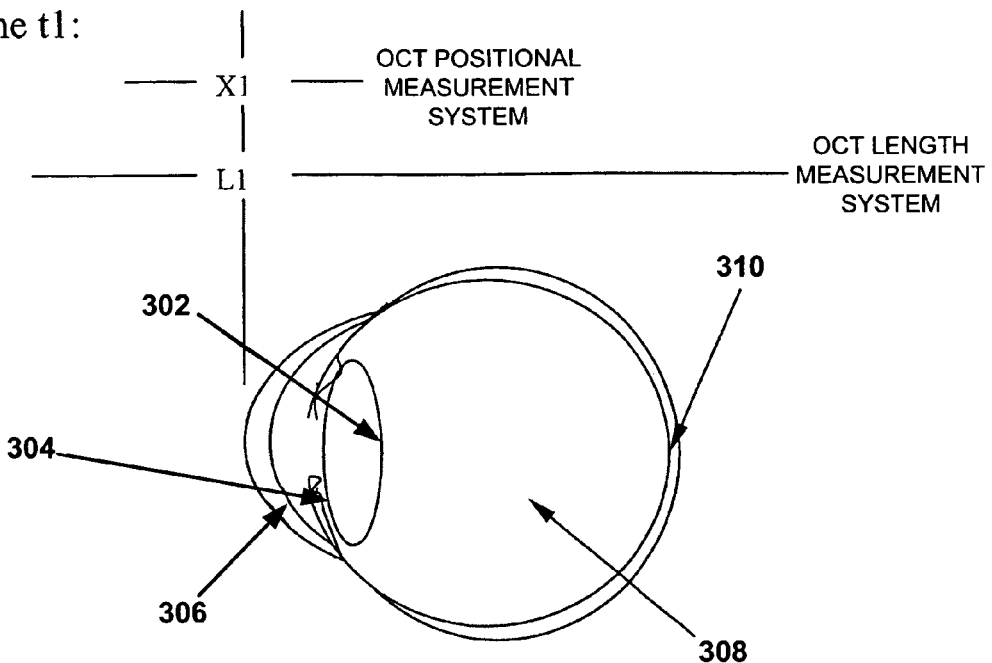
FIGS. 3(a) and 3(b) are diagrams of an eye showing measurement locations that can be used with the system of FIG. 2.
Figure 3B:
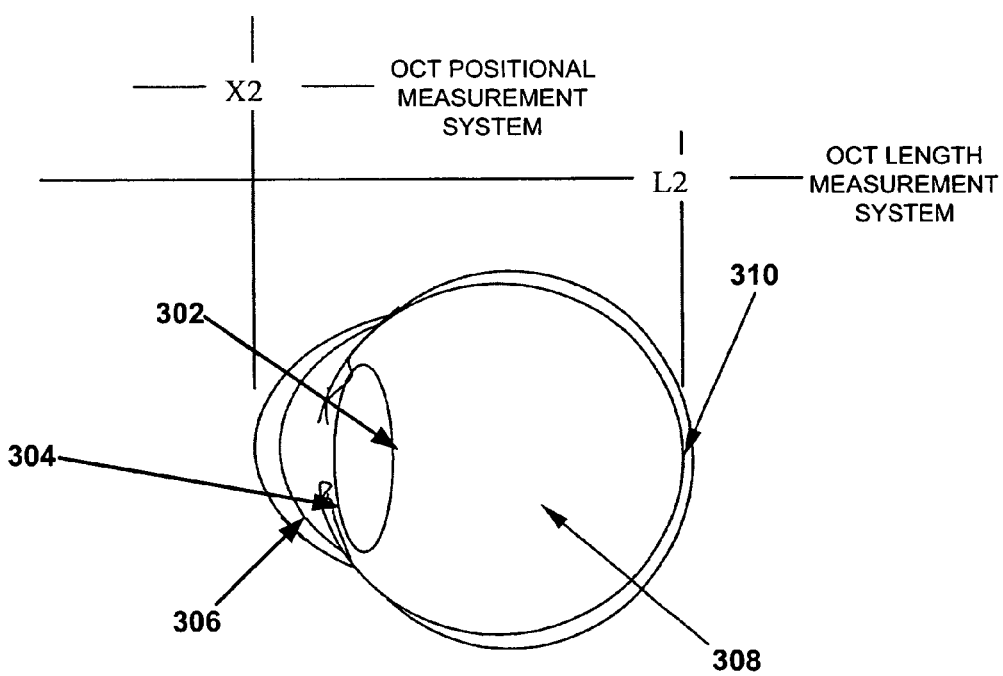
Figure 4:
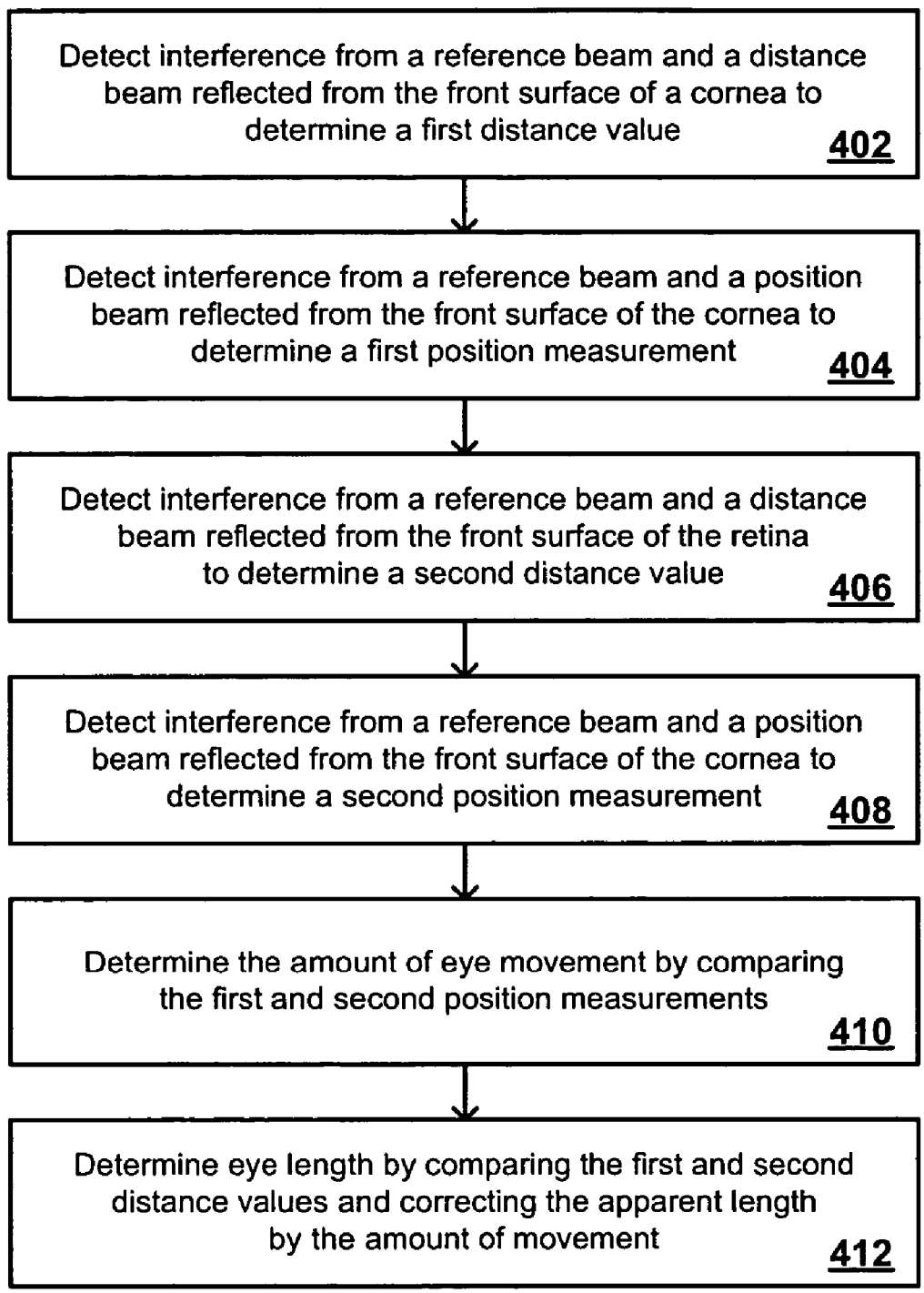
FIG. 4 is a flowchart showing steps of a process that can be used with the system of FIG. 2.

Steps of a process that can be used with the system of FIG. 2 and a measurement technique such as discussed with respect to FIG. 3 are shown in the flowchart 400 of FIG. 4. In such a process, the interference due to a reference beam and a distance beam reflected from the front surface of a cornea is detected to determine a first distance value for the eye 402. At about the same time, such as shortly after the detection for the distance beam, the interference due to another reference beam and a position beam reflected from the front surface of the cornea is detected to determine a first position measurement for the eye 404. At a second time, typically after the measurement of the cornea, a portion of the distance beam is reflected from the front surface of the retina of the eye and the interference due to the reflected reference and distance beams is detected to determine a second distance value for the eye 406. At about the same time, such as shortly after the detection of the distance beam from the retina, the interference due to the other reference beam and the position beam reflected from the front surface of the cornea is detected to determine a second position measurement for the eye 408. The amount of movement of the eye along the measurement path during the measurement period is determined by comparing the first and second position measurements 410. The overall length of the eye is determined by comparing the first and second distance values to determine an apparent length, and adjusting the apparent length by the amount of movement 412. As discussed above, such an approach can be refined through processes such as interpolation and position tracking.

A system in accordance with another embodiment can use the front surface of the cornea as an absolute reference, with the back surface of the eye then being measured relative to the front surface. A potential problem with such an approach is that the front surface of the eye is a much less controlled surface than a reference mirror. The corneal reflection typically is not a well-controlled reflection, such that it does not provide as accurate a reference point as a reference mirror. By contrast, a reference mirror provides an even amount of reflected power and a strong signal, such that the system can be easily optimized. Another advantage to using the reference mirror is that many OCT systems already are generating an image of the cornea, using an absolute reference. Since this monitoring of the front surface exists, it is only necessary to add a system to look for the back surface to determine the eye length. In other embodiments, a technique (such as microscopy) can be used to monitor the position of the cornea, while still using OCT to measure the relative positions of the cornea and retina. Such approaches may not be as accurate as OCT-based systems.

Figure 5:
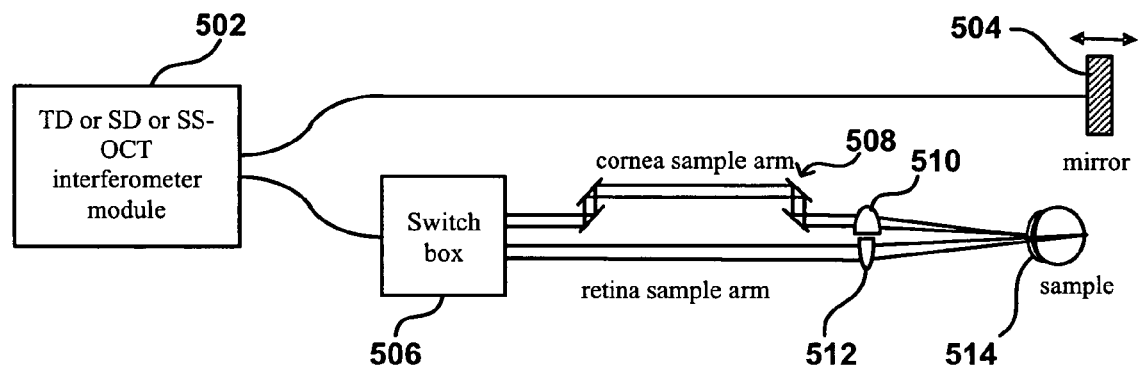
FIG. 5 is a diagram of an OCT system in accordance with another embodiment of the present invention.

A system 500 that can be used in accordance with another embodiment is shown in FIG. 5. In this system, a single OCT module 502, whether TD-, SD-, or SS-OCT, is used to measure eye length. The OCT module can direct light along a single reference arm to a reference mirror 504. For SD- or SS-OCT, the reference mirror can be adjusted to substantially match the position of the cornea (or the retina) and then can be fixed in place. The mirror can be a dithering or other moveable mirror device discussed above for TD-OCT. The OCT module also can direct light along a single sample arm to a switching element such as switch box 506. The switching element can be any appropriate element or device, such as a liquid crystal switch or a lateral transverse scanner, capable of rapidly switching light between two different paths. The switching element in this embodiment can alternately direct the light along a cornea sample path and a retina sample path. The cornea sample path can include at least one optical element 510, such as a focusing lens or mirror, positioned to focus the light onto the front surface of the cornea. The retina path also can have at least one optical element 512 positioned to focus the light onto the front surface of the retina. Since there is only one reference length, the reference length can be set to substantially match the length to the retina. Since the cornea is closer to the switching element, thereby having a shorter effective sample path length, a delay line 508, or optical path extension, can be added to the cornea sample path in order to approximately match the length of the retina sample path (and the reference path length). The delay line 508 can include any elements and configurations known in the art for lengthening an effective light path. The delay line 508 can be adjustable to compensate for different eye lengths, and therefore different retina and reference path lengths. Alternatively, the delay line 508 may be of fixed length, and axial scanning range of the TD-, SD-, or SS-OCT system made sufficiently long to collect reflections both from the cornea through lens 510 and delay line 508, and from the cornea through lens 512, within the axial scanning range.

When using SD- or SS-OCT, an A-scan can be used to capture a full depth (about 3-4 mm) of information about the cornea region when the switch directs light along the cornea sample path. A subsequent A-scan can be used to capture a full depth of information about the retina region when the switch directs light along the retina sample path. The positions of the cornea and retina then can be determined since the reference path length is known. If the switch 506 operates rapidly enough, such as on the order of milliseconds, the eye cannot move more than about 2 microns as discussed above. It is possible when switching that the cornea and retina reflections will overlap, but the relative positions still can be known due to the common reference path length.

When using TD-OCT, the reference mirror typically will need to be scanned as discussed above. The scanning of the reference mirror can be synchronized with the switching element in order to ensure hitting each surface during each scan. In one example, the switching element can be configured to direct the light to the cornea when the mirror is moving along a first scan direction (such as forward), and can be configured to direct light to the retina when the mirror is moving along a second scan direction (such as backward).

It should be mentioned that the switching box can alternatively be placed in the reference arm. In this case the reference path can be split, and the light alternatively directed by the switching box, into a path length that substantially matches the cornea position, and a path length that substantially matches the retina position. The path length differences can be accomplished in one embodiment by using separate reference mirrors that are positioned at different distances relative to the switching box. In an alternative embodiment, a single reference mirror is used and a delay line is placed along one of the measurement paths to the single reference mirror in order to adjust the effective length of the corresponding path.

Figure 6A:
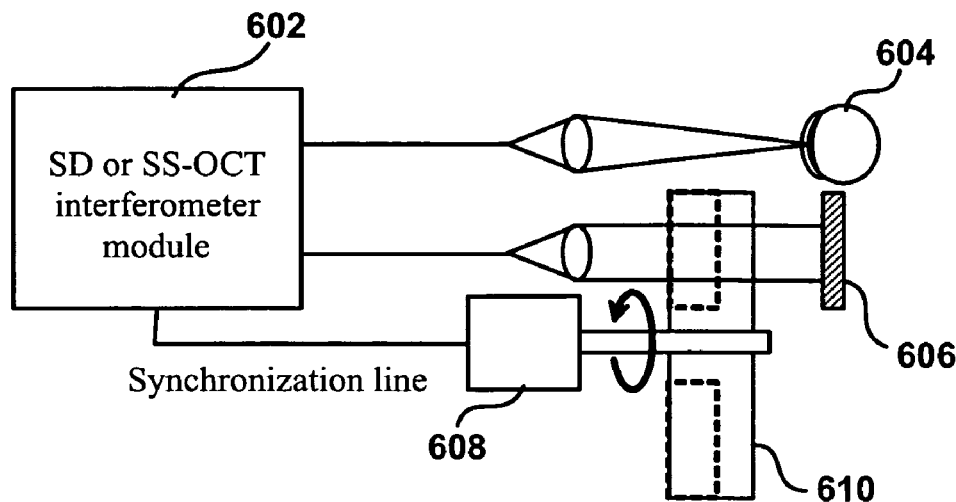
FIG. 6 is a diagram of an OCT system in accordance with another embodiment of the present invention.
Figure 6B:
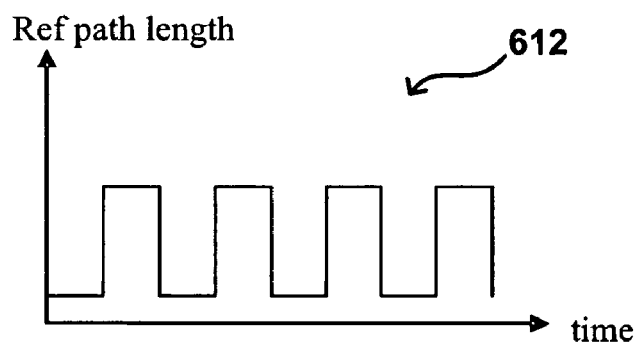
Figure 6C:
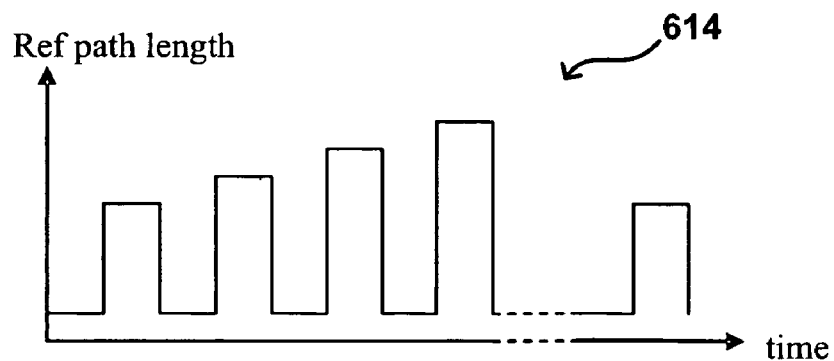

A system 600 that can be used in accordance with another embodiment is shown in FIG. 6(a). This system also uses a single OCT module 602, but it can be desirable to use SD- or SS-OCT since using TD-OCT (and a scanning mirror) may not be very efficient in this configuration. This system again uses a single reference arm and a single sample arm. The OCT module 602 directs light along the sample arm to the eye 604, and along the reference arm to the reference mirror 606. In order to get reference path lengths for both the cornea and the retina, the OCT-module is in communication with a path length altering device, such as a motor device 608 operable to rotate a spinning disk 610 in the path of the reference arm. A spinning disk can have a series of steps that can effectively change the path length of the reference arm, such as is described in U.S. patent application Ser. No. 10/933,795, filed Sep. 3, 2004, which is hereby incorporated herein by reference. The step height can be constant for each step in the spinning disk, such as is shown by the cross-section 612 of FIG. 6(*b*). In this configuration, the step height can be set to effectively match the standard eye length such that the reference path length for the cornea and for the retina can be within the A-scan depth range. The position of the reference mirror 606 can be slowly adjusted to match the position of the cornea using the appropriate step location on the spinning disk, then can be fixed in position. The rotation of the spinning disk can be synchronized with the OCT module such that the appropriate reference path is used during the appropriate scan. A typical A-scan rate can go up to 10 kHz, so the spinning disk should be able to rotate at a rate such that a reference path switch also can occur at that rate. As discussed above, this fast rate only allows for limited movement of the eye. As discussed in the referenced application, the spinning disk also can include reflective elements such that a separate reference mirror is not needed. Other spinning disk and similar path adjusting mechanisms can be used as known in the art.

Since eye length can vary from about 23 mm to about 36 mm, which is a difference greater than the present A-scan depth range, a spinning disk can be used that switches between a set of progressively increasing stepped values. As shown in the cross-section 614 of FIG. 6(*c*), the spinning disk can have differing step heights that can be synchronized with the OCT module, synchronizing with a spectrometer detector array line readout rate or the sweep rate of the swept source, for example. In order to cover the majority of eye lengths, the disk can be configured with step heights (from the cornea step position to the adjacent retina step position) of 21 mm, 25 mm, 29 mm, and 33 mm, for example. The reference path length still can be precisely known for each scan, and the retina can be encountered on every fourth scan regardless of the patient being examined. With a switch rate of 10 kHz, the jump from cornea range to retina range can happen in about 0.1 ms, during which the eye can maximally move only about 0.2 μm. The resultant measurement accuracy will not be appreciably influenced by eye movement.

Figure 7:
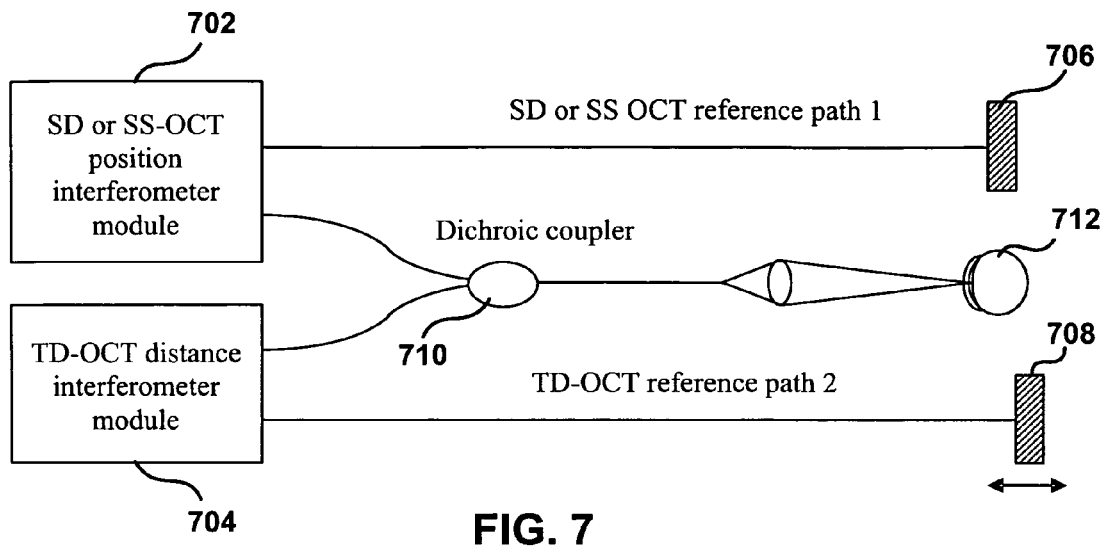
FIG. 7 is a diagram of an OCT system in accordance with another embodiment of the present invention.
Figure 8:
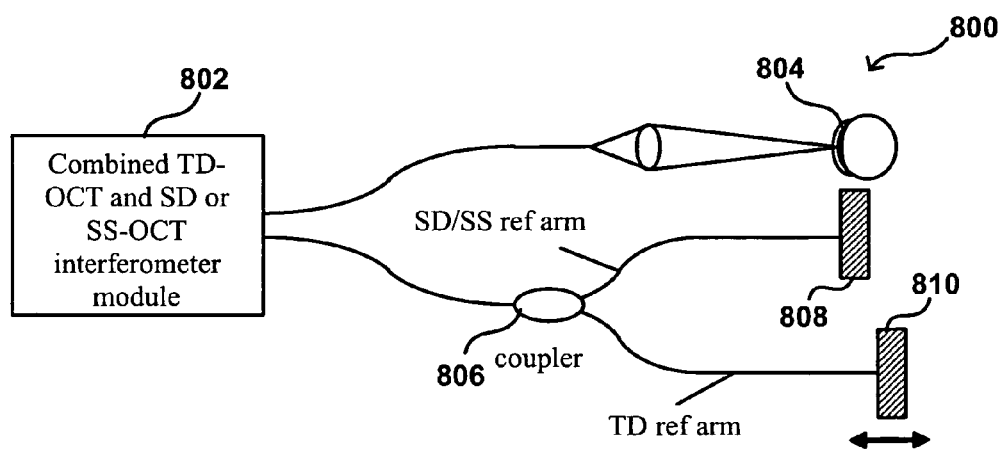
FIG. 8 is a diagram of an OCT system in accordance with another embodiment of the present invention.

A system 700 that can be used in accordance with another embodiment is shown in FIG. 7. This system is similar to the general system described with respect to FIG. 2, except that this specific embodiment utilizes two different types of OCT modules in parallel. In this embodiment a SD- or SS-OCT module 702 is used for measuring cornea position and a TD-OCT module 704 is used for a full length scan of the eye 712. The modules can produce light of two different wavelengths, which can be combined (and subsequently separated) and directed to the eye 712 using an element such as a dichroic coupling element 710. The SD- or SS-OCT module can direct light along a first reference path to a first reference mirror 706, which can be moved initially to capture the location of the cornea then fixed as described above. The SD- or SS-OCT module can use the light of the appropriate wavelength reflected back from the eye through the dichroic coupling element to obtain a quick full depth scan and determine the position of the cornea. The TD-OCT module can direct light along a second reference path to a second reference mirror 708, which can be a slow moving mirror that might take 1-2 seconds to complete a scan and obtain apparent positions of the cornea and retina. Since the position of the cornea is constantly being updated by the SD/SS module, which is much faster than a TD-OCT module, the accuracy of the system can be improved over a system such as the system of FIG. 2 using two TD-OCT modules A system 800 that can be used in accordance with another embodiment is shown in FIG. 8. This system utilizes a single OCT module 802 and a single wavelength (e.g. 850 nm). The OCT module can direct light to the eye 804, as well as to a coupling device 806 capable of splitting the light along two paths then recombining the reflected light. Since some losses might be acceptable in such a system, an ordinary mirror can be used instead of a device such as a dichroic mirror to split a small portion of light in the reference arm to be directed to a second reference mirror 810. The remainder of the light can be directed to a first reference mirror 808. The first reference mirror 808 can be initially adjusted to make the position of the cornea at approximately the middle of the range covered by the SD- or SS-OCT A-scan range, then fixed as discussed above. This first reference mirror can be used to monitor the position of the cornea using an SD- or SS-OCT technique as discussed above. The second reference mirror 810 can be moveable over a larger range in order to generate a TD-OCT scan of either just the retina or a full length of the eye 804. The path length can be mechanically scanned relatively slowly over a large range to cater for the difference of eye length among different patients.

In terms of signal detection and separation, a single SS-OCT detector or a single SD-OCT spectrometer can be used to get both a relatively high frequency signal, which will rapidly reveal the position of the cornea, and also the low frequency signal generated by the Doppler shifted frequency of the TD-OCT subsystem, which can be used to register the position of the retina. An alternative embodiment can utilize two detectors, one detector (such as a spectrometer) for the SD- or SS-OCT signal, and the other detector (such as a photodetector) for TD-OCT signal. The light can be split using any appropriate optical element to direct the light to the appropriate detector. By combining the information from the two signals, an accurate eye length can be obtained while generating an OCT image for the cornea region. It can be more efficient in at least some systems to use a spectrometer to capture and separate both frequencies.

For many such applications it is desired to measure surfaces within 1-10 microns. For many of the systems described herein, particularly the 2 TD-OCT systems case of FIG. 2 the maximum uncertainty in determining the location of the cornea surface by time is $/t_1'-t_1/+/t_2'-t_2/$. In a worst case, this uncertainty will equal twice the scan time of the position measurement OCT reference arm. If the scan rate of this arm is 1000 Hz and the scan range is a few mm, which should cover the largest possible eye axial movement distance, twice the scan time will be 2 ms. The maximum speed of eye movement is 2 mm/s, so the uncertainty of the cornea front surface location determination is (2 mm/s×2 ms), which is 4 microns. This uncertainty is already within the desired range of 1-10 microns. It is possible, however, that there could be some positioning error or drift in the position of the elements of the system, such as the reference mirror(s).

In cases of faster motion of the eye, it could be desirable to reduce a position measurement window down to about 10 to 500 microns instead of a few millimeters (typically about 3 mm) for the determination of the position of the cornea, so that a larger number of measurements can be made per second (for example, 5 kHz instead of 1 kHz) while leaving some margin for positioning error. Furthermore, axial scan apparatuses with lower intrinsic axial-scanning rates have some advantages, the advantages including less-sophisticated mechanism and better sensitivity. The tighter measurement window could allow the intrinsically lower-speed apparatus to reach 1 kHz axial scan rates, due to the shorter scanning range required. A problem with a tight window is that the eye can move such that the surface being measured can be outside the measurement window, whereby no measurement can be made and it can be difficult to relocate the surface. Increasing the window, however, can reduce the measurement rate and decrease the precision in the position measurement. A system in accordance with one embodiment addresses this problem by continually adjusting the position of the window. For instance, if a 10-micron window exists and the position of the front surface of the cornea is measured at 2 microns from one of the "edges" of the window, the window for the next measurement can be shifted by 3 microns in order to center the window around the last measurement and allow for up to 5 microns of movement of the eye in either direction before the next measurement. In a more advanced system, the movement of the eye can be tracked such that a prediction of the next location of the surface can be made based on the last several measurement points, instead of simply the last point. For instance, if the position of the eye were to move back and forth by 8 microns, but always oscillate about the same center point, then simply moving the window by 3-4 microns might allow the surface to be outside the window for the next measurement. By tracking the movement over time, it can be seen that there may be no need to move the window at all. Methods for tracking measurements and making measurement predictions are well known in the art and will not be discussed herein in detail.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

REFERENCES

The following references are hereby incorporated herein by reference.

U.S. Patents
U.S. Pat. No. 4,938,584
U.S. Pat. No. 5,141,302
U.S. Pat. No. 5,321,501
U.S. Pat. No. 5,329,321
U.S. Pat. No. 5,347,327
U.S. Pat. No. 5,347,328
U.S. Pat. No. 5,387,951
U.S. Pat. No. 5,491,524
U.S. Pat. No. 5,633,694
U.S. Pat. No. 5,975,699
U.S. Pat. No. 6,053,613
U.S. Pat. No. 6,775,007
U.S. Published Applications
2005/0140981
2005/0203422
U.S. patent application Ser. No. 10/933,795
PCT Application WO01 38820

Baumgartner, A., et al. (1998). "Signal and Resolution Enhancements in Dual Beam Optical Coherence Tomography of the Human Eye." *Journal of Biomedical Optics* 3(1): 45-54.

Boyle, W. J. O., et al. (1993). "Optical instrumentation for eye length measurement using a short coherence length laser-based interferometer approach." *Review of Scientific Instruments* 64(11): 3082-3087.

Chen, S., et al. (1993). "A compact optical device for eye-length measurement." *Photonics Technology Letters, IEEE* 5(6): 729-731.

Fercher, A. F., et al. (1994). "Measurement of optical distances by optical spectrum modulation". Microscopy, Holography, and Interferometry in Biomedicine, SPIE, 2083: 263-267.

Fercher, A. F., et al. (1988). "Eye-length measurement by interferometry with partially coherent light." *Optics Letters* 13(3): 186-.

Fercher, A. F. and E. Roth (1986). "Ophthalmic laser interferometry". Optical Instrumentation for Biomedical Laser Applications, SPIE, 658: 48-51.

Hellmuth, T. and C. Z. Tan (2001). "Noncontact measurement of the optical imaging quality of an eye". Photon Migration, Optical Coherence Tomography, and Microscopy, SPIE, 4431: 52-58.

Hitzenberger, C. K., M. Kulhavy, et al. (1998). "In-vivo intraocular ranging by wavelength tuning interferometry". Coherence Domain Optical Methods in Biomedical Science and Clinical Applications II, SPIE, 3251: 47-51.

Hitzenberger, C. K., A. F. Fercher, et al. (1991). "Measurement of the axial eye length and retinal thickness by laser Doppler interferometry". Holography, Interferometry, and Optical Pattern Recognition in Biomedicine, SPIE, 1429: 21-25.

Hitzenberger, C. (1991). "Optical measurement of the axial eye length by laser Doppler interferometry." *Invest. Ophthalmol. Vis. Sci.* 32(3): 616-624.

Lexer, F., et al. (1997). "Wavelength-tuning interferometry of intraocular distances." *Applied Optics* 36(25): 6548-6553.

Podoleanu, A. G., et al. (1997). "Fiberised set-up for eye length measurement." *Optics Communications* 137(4-6): 397-405.

Schmid, G. F. (2003). "Axial and peripheral eye length measured with optical low coherence reflectometry." *Journal of Biomedical Optics* 8(4): 655-662.

Sekine, A., et al. (1993). "Axial eye-length measurement by wavelength-shift interferometry." *JOSA A* 10(7): 1651-.

Wang, D. N., et al. (1995). "A low coherence "white light" interferometric sensor for eye length measurement." *Review of Scientific Instruments* 66(12): 5464-5468.

Wang, D. N., G. Dick, et al. (1992). "The Use Of Short Coherence Length Laser Light For Eye Length Measurement". Engineering in Medicine and Biology Society, 1992. Vol. 14. Proceedings of the Annual International Conference of the IEEE, 1: 340-341.

What is claimed is:

1. A system for determining eye length, comprising:
   a first optical coherence interferometer device operable to monitor a position of an eye;
   a second optical coherence interferometer device operable to measure a distance between front and back surfaces of the eye; and
   a processing device in communication with the first and second interferometer devices and operable to determine eye length by correcting the measure of distance, measured by the second interferometer device, by an amount of movement of the position of the eye, measured by the first interferometer device, during the measure of distance by the second interferometer device.

2. A system according to claim 1, wherein:
the first interferometer device includes a light source generating light at about 1300 nm.

3. A system according to claim 1, wherein:
the second interferometer device includes a light source generating light at about 840 nm.

4. A system according to claim 1, wherein:
each of the first and second interferometer devices splits a beam of light into a reference beam directed toward a reference mirror device and a measurement beam directed toward the eye.

5. A system according to claim 4, further comprising:
a combining element operable to combine the measurement beam from each of the first and second interferometer devices to be incident upon the eye along a common path.

6. A system according to claim 5, wherein: the combining element is a dichroic mirror.

7. A system according to claim 4, wherein:
each of the first and second interferometer devices is operable to receive light of an appropriate wavelength reflected from the respective reference mirror device and from the eye.

8. A system according to claim 7, further comprising:
a detector element for each of the first and second interferometer devices operable to measure an intensity of an interference pattern created by the respective interferometer device and generate an output signal in response thereto.

9. A system according to claim 8, further comprising:
a processing device operable to receive the output signal from each of the detector elements for use in determining the distance between front and back surfaces and the movement of the position of the eye.

10. A system according to claim 4, wherein: each reference mirror device produces a variable optical delay.

11. A system according to claim 1, further comprising: a display device operable to receive a display signal from the processing device in order to display the eye length.

12. A system according to claim 1, wherein:
the front surface is a front surface of a cornea of the eye, and the back surface is a front surface of a retina of the eye.

13. A system according to claim 1, wherein:
the processing device is further operable to interpolate between data points captured by the first and second interferometer devices in order to produce a more accurate value of eye length.

14. A system according to claim 1, wherein: the first interferometer device adjusts a measurement window about the front surface of the eye to track movement of the eye.

15. A system for determining length of a moveable object, comprising:
means for monitoring a position of the moveable object;
means for measuring an apparent axial distance between first and second surfaces of the moveable object; and
means for determining a corrected axial distance between the first and second surfaces of the moveable object by correcting the measure of apparent axial distance by an amount of movement of the position of the moveable object during measurement of the distance between first and second surfaces.

16. A method for determining eye length, comprising:
monitoring a position of an eye using a first optical coherence interferometer device;
measuring a distance between front and back surfaces of the eye using a second optical coherence interferometer device; and
determining eye length by correcting the measure of distance, measured by the second interferometer device, by an amount of movement of the position of the eye, measured by the first interferometer device, during the measure of distance by the second interferometer device.

17. A method according to claim 16, wherein:
monitoring a position of an eye using a first interferometer device includes directing a first portion of a beam of 1300 nm light to a reference mirror device and a second portion to the eye being measured.

18. A method according to claim 17, wherein:
monitoring a position of an eye using a first interferometer device further includes receiving reflected first and second portions to an interferometer and measuring an intensity of the interference pattern.

19. A method according to claim 16, wherein:
measuring a distance between front and back surfaces using a second interferometer device includes directing a first portion of a beam of 840 nm light to a reference mirror device and a second portion to the eye being measured.

20. A method according to claim 19, wherein:
measuring a distance between front and back surfaces using a second interferometer device further includes receiving reflected first and second portions to an interferometer and measuring an intensity of the interference pattern.

21. A method according to claim 16, further comprising:
combining a measurement beam for each of the first and second interferometer devices to be incident upon the eye along a common path.

22. A method according to claim 16, further comprising:
generating a variable optical delay for each of the first and second interferometer devices.

23. A method according to claim 16, wherein:
the front surface is a front surface of a cornea of the eye, and the back surface is a front surface of a retina of the eye.

24. A method according to claim 16, further comprising:
interpolating between data points captured by the first and second interferometer devices in order to produce a more accurate value of eye length.

25. A method according to claim 16, further comprising:
adjusting a measurement window of the first interferometer device about the front surface of the eye to track movement of the eye.

* * * * *